United States Patent [19]

Eisinger et al.

[11] Patent Number: 4,943,522
[45] Date of Patent: Jul. 24, 1990

[54] LATERAL FLOW, NON-BIBULOUS MEMBRANE ASSAY PROTOCOLS

[75] Inventors: Robert W. Eisinger; Mohammed H. Khalil, both of San Diego; David H. Katz, La Jolla; Robert B. Sargeant, Ramona, all of Calif.

[73] Assignee: Quidel, San Diego, Calif.

[21] Appl. No.: 230,642

[22] Filed: Aug. 10, 1988

Related U.S. Application Data

[63] Continuation-in-part of Ser. No. 57,273, Jun. 1, 1987, abandoned, and a continuation-in-part of Ser. No. 57,271, Jun. 1, 1987, abandoned.

[51] Int. Cl.$^5$ ............................................. G01N 33/53
[52] U.S. Cl. .......................................... 435/7; 435/805; 435/810; 436/512; 436/514; 436/518; 436/520; 436/523; 436/531; 436/535; 436/807; 436/808; 436/810; 422/55; 422/56; 422/57; 422/58; 422/101
[58] Field of Search .................................. 422/55-61, 422/70, 101, 102; 424/11; 435/7, 5, 805, 810; 436/514-520, 512, 523, 531, 535, 807, 808, 810; 210/431

[56] References Cited

U.S. PATENT DOCUMENTS

| | | | |
|---|---|---|---|
| 4,323,536 | 4/1982 | Columbus | 422/56 |
| 4,361,537 | 11/1982 | Deutsch et al. | 422/56 |
| 4,608,246 | 8/1986 | Bayer et al. | 424/11 |
| 4,623,461 | 11/1986 | Hossom et al. | 422/101 X |
| 4,693,834 | 9/1987 | Hossom et al. | 422/101 X |
| 4,729,961 | 3/1988 | Avrameas et al. | 435/7 X |
| 4,740,475 | 4/1988 | Paul | 422/58 X |

FOREIGN PATENT DOCUMENTS

| | | | |
|---|---|---|---|
| 0209378 | 1/1987 | European Pat. Off. | 436/518 |
| 8803650 | 5/1988 | World Int. Prop. O. | 436/518 |

Primary Examiner—Esther M. Kepplinger
Assistant Examiner—Carol A. Spiegel
Attorney, Agent, or Firm—Irell & Manella

[57] ABSTRACT

A method and apparatus for conducting specific binding pair assays, such as immunoassays, is described. A porous membrane capable of non-bibulous lateral flow is used as assay substrate; a member of the binding pair is affixed in an indicator zone defined in the substrate. The sample is applied at a position distant from the indicator zone and permitted to flow laterally through the zone; any analyte in the sample is complexed by the affixed specific binding member, and detected. A novel method of detection employs entrapment of observable particle in the complex. Blood is a particularly preferred sample as the red blood cells can be used as the observable particles for detection of the complex.

46 Claims, 4 Drawing Sheets

LATERAL FLOW, NON-BIBULOUS MEMBRANE ASSAY PROTOCOLS

This is a continuation-in-part of copending application Ser. Nos. 057,273 and 057,271, both filed June 1, 1987, and now abandoned.

FIELD OF THE INVENTION

This invention relates to immunological and related assay methods and apparatus, especially to those for blood testing.

BACKGROUND OF THE INVENTION

The technology of specific binding diagnostic reactions and reagents generally has developed rapidly in the past two decades, and continues to develop at a rapid pace. Radiommunoassays (RIAs) and enzyme-linked immunosorbent assays (ELISAs), for example, have become widely known and are described in numerous tests, treatises, scientific papers and patents. ELISAs have become commonplace and achieved great importance in medicine and in scientific research since the pioneering work begun by Engvall, E., and Perlmann, P., et al, *Immunochem* (1971) 8:871–874; and the work of Schuurs and coworkers; see, e.g., Van Weemen, *FEBS Letters* (1971) 15:232–236, and several U.S. Patents naming Schuurs et al as inventors; see, e.g., U.S. Pat. Nos. Re. 31,006, 3,654,090, 3,839,153, 3,850,752, 3,862,302, 3,862,928, 3,879,262, and 4,016,043. Monoclonal antibodies in enzyme immunoassays are well known; see, e.g., the work of Herzenberg and of Engvall, and others and the later work of David et al, U.S. Pat. No. 4,376,110. DNA probes and biochemical and biological probes generally exhibit the ability to bind specifically and are of great current interest as specific binding pairs.

*ENZYME IMMUNOASSAY*, Ishikawa, M. D., Tadashi, Kawai, and Kiyoshi, Miyai, eds, IGAKU-SHOIN, New York 1981, describes in considerable fundamental detail the principles and practices involved in enzyme immunoassays. Reference is also made to other texts and treatises in the field, such as *IMMUNOCHEMICAL METHODS IN THE BIOLOGICAL SCIENCES: ENZYMES AND PROTEINS*, Mayer, R. J., and Walker, J. H., Academic Press, New York 1980; *QUANTITATIVE ENZYME IMMUNOASSAY*, Engvall, E., and Pesce, A. J., Blackwell Scientific Publications, London (Scandinavian Journal of Immunology, 1978); *THE ENZYME LINKED IMMUNOSORBENT ASSAY (ELISA) A guide with abstracts of microplate applications*, Voller, A., Bidwell, D. E., and Bartlett, A., Dynatech Laboratories, Inc., 1979; and the references cited therein for a comprehensive disclosure of the principles and usual practices involved in enzyme immunoassay.

Various approaches have been described for carrying out enzyme immunoassays. The early ELISAs were what is commonly called a "competitive" assay in which the enzyme labeled antigen or antibody competed with the antigen or antibody to be determined for a reaction site on a bead, pad or surface to which one member of an immunologically coupling pair was attached. Later, the "sandwich" assay became popular. In the sandwich assay, the antibody or antigen to be determined was "sandwiched" by an immunochemical reaction between a solid surface treated with an immunological species reactive with the species to be determined and the same or a different reactive immunological species which has been coupled to an enzyme label. The principles of these types of ELISAs are discussed by Belanger, L., *Scand J Immunol*, (1978) 8:Suppl. 7, 33–41; (Chapter 4 in *QUANTITATIVE ENZYME IMMUNOASSAY*, supra).

Many forms of solid supports to which one member of an immunochemical couple, e.g., antigen-antibody or hapten-antibody couple, have been disclosed. A common early form of solid support was a plate, tube or bead of polystyrene which was well-known from radioimmunoassay (RIA) work to bind certain immunological species. Filter paper, glass, various plastics (chemical polymers), and other solid support surfaces have been used for many years. Examples of such a system which used antibody (or antigen) coated polystyrene beads are described by Bohn et al, in U.S. Pat. No. 4,424,279, Jan. 3, 1984; and U.S. Pat. No. 4,458,020, July 3, 1984, in which the coated beads are utilized in unique configurations.

Several disclosures are directed to assays which employ passage of the sample to be tested through a solid membrane or support.

Tom et al, U.S. Pat. No. 4,366,241, disclose an apparatus for an immunoassay which includes a multiple layered construction in which the sample solution flows into an enclosure through an immunoabsorbing disk which has antibody or antigen bound to it. The solution flows from the disk through a membrane spacer which is in contact with the disk and into a bibulous strip of cellulose or paper which extends through the enclosure to a level above the sample into which the apparatus is inserted during use.

U.S. Pat. No. 4,632,901, to Valkirs et al, discloses a device and method for immunoassays in which the sample flows through the thickness of a membrane to an absorbent mass. Antibody is bound to less than the total surface of the membrane and binds antigen in the antibody coated area. Conventional ELISA techniques are used to detect the sample bound to the supported antibody.

Various configurations for self-contained assay systems have also been described; for example, Deutsch, A., and Platt, H. A., U.S. Pat. No. 4,522,923, describe a device which comprises a container, at least two water-soluble barriers, subdividing the container into at least three superimposed chambers, and different biologically active substances in each chamber. Upon introduction of an aqueous biological sample to be tested into the topmost chamber, the sample successively mixes with the contents of the chambers, the contact time in each chamber being a function of the water solubility of the barriers. The system is designed to give a color reading in the final chamber. This provides a method for conducting immunochemical reactions in a self-contained sealed unit that requires only the addition of an unknown sample and water, and thus provides an assay system that is safe and accurate even when used by an individual who is not technically trained. Specifically at least one chamber contains an antigen, antibody, or an enzyme, or their conjugates. Preferably the antibody is directed against human chorionic gonadotropin hormone. Specifically the substances in the chambers represent color-change immunochemical reactions, e.g., home testing of blood or urine for pregnancy.

Barnett, B., W08606488, describes a diagnostic test kit which has a central well for receiving a sample to be analyzed. Several reservoirs holding predetermined quantities of reagents are located in a block which surrounds the sample well and are connected to it via bores. Initially the reagents are retained in the respective reservoirs by membranes but the contents of a reservoir can be discharged by rupturing the membrane. The reservoirs are formed by resilient domes which are depressed manually to rupture the membrane and serve to transfer the reagent to the sample well. The test kit is used for screening, chemical or clinical analysis of blood, urine, swimming pool water, drinking water or soil. The test kit reduces the chance of human error in the sequential addition of reagents to a sample.

Graham, H. A., Olekna, D. J., Hawk, J. B., and Kebles, D. B., EP0022669, describe a test in which red blood cells are rapidly tested for the presence of antigens O, C, c, E, e or K by mixing them with an antibody reagent (A) and, without incubation, examining them for agglutination. (A) comprises reduced S-alkylated IgG antibody against the appropriate antigen which at least meets FDA standards for potency and specificity.

Deutsch, M. E., and Mead, L. W., U.S. Pat. Nos. 4,094,647, 4,235,601 and 4,361,537, describe a test strip for determining a characteristic of a sample comprises a length of material capable of transporting a developing liquid by capillarity and having zones between its ends for receiving the sample and holding reagents. The strip is used for performing binding assays, particularly those in which a radioisotope is used as a label, such as radioimmunoassays. Minute sample sizes may be used. The strip is capable of application to analytical methods having sensitivities below 0.1 mg/ml.

Friedenberg, R. M., FR 2537724, describes a dry indicator apparatus for drugs-of-abuse testing of physiological liquid test solutions. A non-bibulous capillary flow membrane vehicle matrix is impregnated with dry chemical colorants. When these are placed in contact with the test solution the colored reagent indicates the type of drug present even in low concentrations. The test is a qualitative and quantitative indicator for the presence of abused drugs, such as barbiturates, amphetamines, methadone, morphine, cocaine, codeine, dilaulid and tranquilizers of the diazepam type. The physiological fluids tested include urine, whole blood, plasma, sweat and tears.

Lipp, V., and Buck, R. L., EP 0206779, describe an apparatus for detecting antinuclear antibody in a biological sample comprising a solid support having adhered nuclei isolated from eucaryotic cells. Preferably underlying the nuclei on the solid support is a coating, e.g., of nuclear antigens, which is unreactive with antibodies to non-nuclear antigens and which, like nuclei serves to bind antinuclear antibodies in the sample. The apparatus permits the screening of human serum for the presence of antinuclear antibodies in a system featuring speed, simplicity, sensitivity and capacity for automation. Medical disorders characterized by the presence of antinuclear antibodies include systemic lupus erythematosus, mixed connective tissue disease, Sjogren's syndrome and scleroderma.

Deutsch, A., Sheets, E. J., and Rhodes, J., EP 0189925, describe a kit which comprises (a) a vessel, (b) a capillary-active wick extending from the interior of the vessel so as to wick a liquid out of the interior of the vessel, a portion of the wick carrying an immobilized immunological component selected from (i) antigen and (ii) antibody, (c) a first reagent comprising an enzyme conjugated to an immunological component selected from (i) antibody and (ii) antigen specific to (i) or (ii) respectively of (b) and (d) a substrate for the enzyme. In place of the enzyme and substrate a fluorescent label may be used. Antigens which can be tested for include dilantin, testosterone and progesterone. If the sample contains the antigen, it will combine with the antibody-enzyme while moving along the wick so that when this mixture subsequently wicks through the antigen-wick, there will be no free antibody-enzyme to bind to the antigen on the wick so it will pass out of the wick.

Friedenberg, WPO Int. Pub. No. WO 84/02397, also describes an immunoassay in which the reactions occur in the liquid phase as the sample moves through a paper support, the rate of movement being one parameter used in identifying constituents.

Campbell, U.S. Pat. No. 3,893,808, describes a strip of filter paper treated in bands with a chemical reagent, iodine, into which a sample of gasoline suspected of containing lead is wicked from one end and a developing reagent, dithizone, is wicked into the pretreated bands.

Alberty et al, U.S. Pat. No. 3,895,914, describe another chemically treated test strip in which chemical reagents are applied in bands or zones on a strip for detecting barbituric acid.

While the prior art teaches the use of wicking bibulous materials as carriers for specific binding reagents, these apparatus and methods rely principally upon the ability of the carrier to imbibe the liquid and often to enter into the reaction. The use of bibulous materials is of great value in some methods, but presents serious limitations as well, in reduced sensitivity and in the nature of the reagents and analytes which may be used or determined. The present invention utilizes a non-bibulous material in which the liquid flow is isotropic and flows laterally in the material by capillary action, thus presenting a system in which the solid membrane provides a vessel for the liquid but does not imbibe or otherwise enter into or interfere with the specific binding reactions.

DISCLOSURE OF THE INVENTION

The invention provides a method and apparatus for determining the presence or absence or the amount of analyte using a specific binding assay. The apparatus comprises a non-bibulous lateral flow membrane which has on its surface a sample application zone to receive a liquid sample, and, at a lateral distance from the application zone on the surface, at least one indicator zone. In the indicator zone is affixed a member of a binding pair; the sample contains an analyte which is its complementary binding member or an analyte which can be derivatized so as to bind the fixed member. In one convenient configuration the membrane is bound to two substantially fluid-impervious sheets, one on either side, with openings on one side or both sides to provide definition to the application and indicator zones.

The lateral flow achieved in the method of the invention is the result of the properties of the non-bibulous lateral flow membrane. The membrane has a much smaller thickness than surface dimension and is hydrophilic enough to be wetted and thus permit aqueous solutions and materials to exhibit lateral flow freely, and preferably isotropically, at substantially the same rates for various components of a sample.

Thus, in one aspect, the invention is directed to an apparatus for assaying an analyte in a sample to be tested by a specific binding reaction which apparatus comprises a non-bibulous lateral flow membrane, said membrane having at least one sample application zone and at least one indicator zone, said zones laterally separated, and wherein in the indicator zone is affixed a member of a binding pair.

The apparatus may further comprise one or more breakable containers of buffers or reagents positioned in a holder adjacent the membrane. These can be broken by a means which may also be included in the holder, to provide needed developing reagents or wash solutions to the indicator zone when the container is broken. Another aspect of the invention comprises such designs.

The membrane may include more than one indicator zone, along with control and reference zones. Multiple indicator zones may be designed to detect different analytes or for quantifying the amount of analyte. Multiple indicator zones may be in any spaced relationship to the application zone, since the membrane itself does not provide a barrier to sample flow.

In the method of the invention, the sample, which contains an analyte which is, or which can be derivatized to include, a first member of a binding pair, is applied to the application zone and allowed to be transported laterally through the membrane to an indicator zone, where there is, affixed to the membrane, the other, second, member of the binding pair. The first member binds, in the indicator zone, to the second member, and the resulting bound complex is detected. Detection may use any of a variety of labels and/or markers, e.g., enzymes, radioisotopes, liposomes, fluorescent tags, polymer dyes, or colored particles, etc., and detection is by means of, for example, direct visual observation, by developing a color, by radioactive isotope counting, by fluorescence measurement, or by any of many other techniques by which the presence or absence of a chemical or biochemical species may be detected directly or indirectly.

In one preferred embodiment, and an additional aspect of the invention, visible particles in, added to, or applied before or after, the sample are used for detection by being trapped in the indicator zone by the binding pair complex. If the analyte itself provides a visible particle, for example, in the case of analyte being an antigen present on red blood cells, which cells can be seen directly, no separate detection means is needed. If the visible particles reside in the sample, e.g., the red blood cells in whole blood will remain in the indicator zone after washing when the binding complex is formed.

Thus, in another aspect, the invention is directed to a method to detect the formation of a complex between a first binding reaction pair member from a sample and the second member of the pair affixed in an indicator zone, which method comprises supplying, along with or after the sample, detectable particulates which are entrapped by the complex and thus detected in the indicator zone. The particles may occur naturally in the sample as is the case for the red blood cells in whole blood. In other instances, the particles may be added artificially.

In another aspect, the invention is directed to a method of blood typing using the membrane described. A blood sample is applied to the application zone and permitted to flow through the membrane to one or more indicator zones, each of which contains a blood typing reagent, such as an antibody to group A antigen, to group B antigen or to Rh factor. The blood sample is then washed through the membrane so that the red blood cells remain visible only in the indicator zones which contain the specific binding member of the pair pertinent to an antigen present in the sample. Thus, for example, type A blood will be visible in an indicator zone containing anti-A; blood lacking this antigen will be removed from this zone, which will appear clear.

In other aspects, the invention relates to specific configurations of the application and indicator zones on the membrane.

MODES OF CARRYING OUT THE INVENTION

General Description

Figure 1:
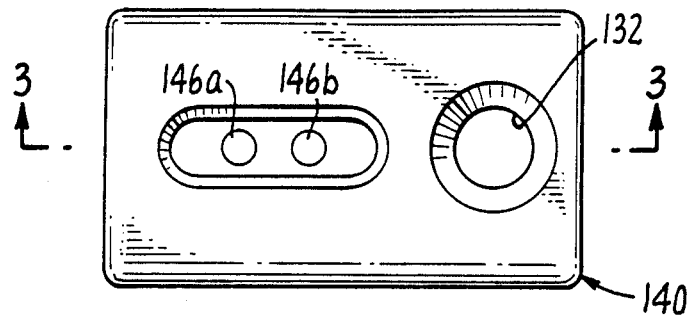
FIG. 1 is a top plan view of the holder in a preferred embodiment of the invention.

An essential feature of the invention is the employment of a membrane capable of non-bibulous lateral flow. By "non-bibulous" lateral flow is meant liquid flow in which all of the dissolved or dispersed components of the liquid are carried at substantially equal rates and with relatively unimpaired flow laterally through the membrane, as opposed to preferential retention of one or more components as would occur, for example, in materials capable of adsorbing or "imbibing" one or more components. "Bibulous" materials include paper, nitrocellulose, nylon and the like, which have the capability to effect a chromatographic separation of the contained materials.

An example of the membrane material in which capillary, non-bibulous lateral flow occurs is the high density or ultra high molecular weight polyethylene sheet material manufactured by Porex Technologies Corp. of Fairburn, Georgia, USA. This membrane has an open pore structure with a typical density, at 40% void volume, of 0.57 gm/cc and an average pore diameter of 1 to 250 micrometers, the average generally being from 3 to 100 micrometers. The optimum pore diameter for the membrane for use in the invention is about 10 to about 50 $\mu$m. The membranes are from a few mils (0.001 in) to several mils in thickness, typically in the range of from 5 or 10 mils and up to 200 mils. The membrane may be backed with a generally water impervious layer, or may be totally free standing. While membranes made of polyethylene have been found to be highly satisfactory, lateral flow, non-bibulous membranes formed of other olefin or other thermoplastic materials, e.g., polyvinyl chloride, polyvinyl acetate, copolymers of vinyl acetate and vinyl chloride, polyamide, polycarbonate, polystyrene, etc., can be used. Membranes formed by the classical phase inversion process may also be used.

Thus, the membranes, in general, will have a pore size of about 3-100 μm, preferably about 10-50 μm; will be constructed of an inert material; and will be less than 200 mils in thickness. They are characterized by non-bibulous lateral flow. Isotropic flow is preferred. While applicants believe this lateral flow to be caused, at least in part, by capillary action, they are not bound by any particular theory to explain the characteristic nature of this non-chromatographic flow.

In the various apparatus and method embodiments of the invention, the lateral flow non-bibulous membrane will contain an application zone and at least one indicator zone, wherein the indicator zone has affixed to it a member of a binding pair. The membrane may be in any desired shape and the application and indicator zone may have any desired configuration as is convenient for use alone or in a particular apparatus.

To the indicator zone in the apparatus and method of the invention is affixed one of the members of a binding pair, which is responsible for the capture of its complementary member. By "affixed" in this context is meant retained in the indicator zone throughout the assay procedure—this can be accomplished by covalent bonding or, more commonly, by adsorption, e.g., by drying. Depending on the nature of the material comprising the membrane, derivatization to permit covalent bonding for example, using glutaraldehyde or a carbodiimide, can be employed.

Most binding pairs employed in the invention are "specific", e.g., antigen-antibody pairs, and other specific coupling pairs such as antibody-hapten, antibody-cell, antibody-cell fragment, RNA and DNA probes, receptor-receptor ligand, enzyme-substrate, enzyme-inhibitor and other pairs in which a specific binding reaction occurs. However, in some instances the specificity of the assay may be conferred in other ways, such as by a labeling reagent. The requirement for the affixed member is that it must bind the analyte or its derivative. Thus, one of the members of the coupling pair is affixed physically, chemically, biologically or otherwise to the non-bibulous lateral flow membrane indicator zone to bind the other member of the pair.

The affixed member of the pair may bind directly to the analyte, or may bind to a derivative thereof. By "derivative" is meant any substance whose concentration in the sample is directly proportional to analyte. For example, the derivative may be a conjugate of the analyte with an additional component which, in turn, binds to the affixed member, or with an additional component which serves merely to label the analyte, but not interfere with the analyte's ability to bind to the affixed member. In another illustration, the derivative might be a reaction product formed in stoichiometric relationship to analyte in a reaction, wherein the reaction product binds to the affixed member. Thus, "derivative" is a substance quantitatively related to analyte concentration.

It is not necessary that the binding pair member be bound directly, chemically or biologically to the membrane. The binding pair member may be attached to another material wherein said material is physically entrapped in the indicator zone or otherwise affixed in the indicator zone by any physical, chemical or biochemical means. For example, specific binding members can be attached covalently or passively to beads or the like and the beads then affixed on the membrane.

The method of the invention is conducted by applying a liquid sample to the application zone at the surface of the membrane in sufficient quantity to permit the sample to flow through at least one, or through at least as many indicator zones as desired. Control and blank zones may also be defined to receive the sample flow. Flow will occur laterally through the membrane due to its intrinsic properties; while applicants believe this is due to capillary action, there is no intent to be bound to any particular theory or explanation. If, along the direction of flow, the membrane terminates at the indicator zone, the liquid may flow out of the membrane; if there is additional surface beyond the indicator zone in the direction of flow, this surface will act as an "absorbent" zone, and further encourage the flow of liquid. A bibulous or nonbibulous material may also be placed in contact with the membrane to act as additional absorbent.

In the method, then, the sample flows from the application zone through the indicator zone and, if applicable, into the absorbent zone. The presence of analyte in the sample will cause a detectable reaction in the indicator zone.

The experimental design protocol or "chemistry" of the assays of the invention can be varied as is generally known for assays based on specific binding. Most of the protocols adapted to other physical formats of immunoassay can be used in the apparatus of the invention, where the indicator zone fills the role of the binding member bound to solid support. For example:

(1) Analyte in the sample binds specifically to the member affixed to the indicator zone; a label is then added to detect the bound analyte; i.e., in a sandwich immunoassay;

(2) The sample is spiked with a labeled form of analyte and the labeled form bound to the member affixed in the indicator zone is detected—i.e., a competition assay;

(3) Analyte carries with it the means of its own detection—the most notable example being analyte conjugated to an observable particle. Also, the analyte may first be reacted with label, for example, with an antibody conjugated to enzyme. The label-bearing analyte can then be bound specifically to the affixed member. In an alternative, a labeled analyte may be bound to a specific counterpart which is the complement to the fixed member. For example, red blood cell-borne analyte may be reacted with murine anti-antigen to form a complex, which is then bound to rabbit antimurine Ig affixed in the indicator zone;

(4) Detectable particles may be used to detect an unlabeled complex of analyte with binding pair member in the indicator zone.

Typical Analytes

The analyte may be insoluble or attached to insoluble supports or may be soluble.

Typical cell-bound or solid supported analytes include, e.g.,

Tissue-Specific Cell Surface Markers: Separation of cell populations based on these markers has been performed using lectins (Reisner and Sharon, *Trends in Biochem Sci* (TIBS) 29, 1980), blood leukocyte surface glycoproteins (Gahmberg and Anderssen, *NYAS* (1978) 312, in *Fibroblast Surface Proteins* eds. Vahery, Ruslahti and Mosher), estrogen steroid receptors (Thompson, *Cancer Treatment Reports* (1978) 63(2) 180, erythrocyte insulin receptors (Bhathena et al, *Horm Metab Res* (1981) 13:179), or multiple markers as in the case of lymphocytes. Further separation of subpopulations is possible based on markers identified with specific cell functions as in the case of the T lymphocytes (Reinberg and Schlossman, *N Eng J Med* (1980) 303:1153).

Tissue-Shared Cell Surface Markers: Some cell surface markers are present on multiple cell types. An example of these are the Major Histocompatibility Complex Human Lymphocyte Antigen (HLA) system, LETS protein, p glycoprotein (Kartner et al, *Science* (1983) 221:1285) and transferrin receptors (Omary et al, *Nature* (London) (1980) 286:888).

Viral-Associated Cell Surface Markers: Cell membrane antigens can also result from viral infection. The mumps H—N glycoprotein detectable by RIA, immunofluorescence and hemagglutination inhibition represents a viral marker on infected cells (Sever et al, *Infect & Immun* (1982) 35(1):179). Similarly, markers resulting from Herpes Simplex 1 and 2 infection are recognizable on the host cell surface by immunofluorescence (Stewart and Herrmann, "Herpes Simplex Virus" in *Manual of Clinical Immunology*, 2nd edition, edited by N. R. Rose and H. Friedman, American Society for Microbiology, Washington, D.C., 1980).

Tumor-Specific Cell Surface Markers: Neoplastic and oncogenic transformation results in the alteration of the cell phenotype as expressed in cell surface proteins. These can be observed as variations in the presence of cell surface antigens normally expressed on the cell surface, appearance of "altered self antigens," appearance of embryonic cell surface antigens and the presence of tumor specific molecules. Felsted et al (*Canc Res* (1983) 43:2754) have described cell membrane changes during the differentiation of promyelocytic leukemia cells. Neoplastic transformation induced changes in cell phenotype are presented in a review by Poste (in *Cancer Invasion and Metastasis: Biologic Mechanisms and Therapy* edited by S. B. Day et al, Raven Press, New York, 1977). Similar review articles describe phenotypes of leukemic cells (Greaves et al in *Proc of International Symposium on Human Lymphocyte Differentiation: Its Application to Cancer*, edited by Seron and Rosenfeld, North Holland Publishing, Amsterdam, 1978), B Lymphocytes (Thorsky et al, IBID), and Acute Lymphocytic Leukemia Cells (Greaves et al, *Science* 234, 1986).

The identification of tumor specific antigens or markers and their association with tumors of specific tissue types permits clearer diagnosis and subsequent monitoring during therapy. A number of tumor surface proteins have been identified. Several examples include: a mutated rat gene p21 tumor lymphocyte protein (Bos et al, *Nature* (London) (1985) 315:726, and Clark et al, *PNAS* (USA) (1985) 82:5280); an Acute Lymphocyte Leukemia (ALL) Associated antigen GP 100 Ph1 (Greaves et al, *Blood* (1983) 61:628); Human T cell Leukemia Associated Antigen (HTLA) (Seon et al, *J of Immunol* (1981) 127(6):2580); a Human Lung Tumor Associated Antigen (Braatz et al, *J Nat Cancer Inst* (1978) 61(4):1035), an estrogen 24,000 MW Human breast cancer marker (Adams et al, *Cancer Res* (1983) 43:4297); a Human Leiomyosarcoma antigen (Deng et al, *Lancet*, Feb. 21, 1981, p. 403); and a Human Mammary carcinoma antigen (Schlom et al, *PNAS* (1980) 77 (11):6841).

Further concerning tumor markers, the concept of "altered self antigens" proposed by Edelman, *Science* (1976) 197:218 describes the presence of modified cell surface antigens normally indigenous to a cell type which are altered due to neoplastic transformation. These aberrant cells are viewed by the immune surveillance system as abnormal and they are capable of eliciting an immune response (Burnet, *Brit Med J* (1957) 1:179, and *Nature* (1970) 226:123). The reappearance of embryonic antigens have also been observed following the neoplastic transformation of cells. Carcinoembryonic antigen (CEA), Fetal Embryonic antigen (FEA) and Tumor Specific Transplantation Antigens (TSTA) have been useful in the serodiagnostic detection of carcinomas and sarcomas (Mitchison, "Immune Surveillance" in *B and T Cells in Immune Recognition* edited by F. Loors and G. E. Roelants, Wiley and Sons, New York, 1977).

A preferred analyte is the set of antigens found on red blood cells, wherein the cells themselves can serve as markers.

In addition to surface markers, soluble analytes can also be detected and measured. Typical soluble analytes include: hormones, enzymes, lipoproteins, viral antigens, immunoglobulins, lymphokines, cytokines, drugs, soluble cancer antigens, bacterial antigens and the like. These analytes include various proteins such as protamines, histones, phosphorylated proteins, nucleoproteins, and so forth such as, for example, transcortin, erythropoeitin, transferrin, various globulins, thyroxin-binding globulin, the immunoglobulins of various subclasses A, G, D, E, and M, various complement factors, blood clotting factors such as fibrinogen, Factor VIII, tissue thromboplastin, and thrombin.

Also included are hormones such as insulin, glucagon, relaxin, thyrotropin, somatotropin, gonadotropin, follicle-stimulating hormone, gastrin, bradykinin, vasopressin, and various releasing factors. A wide range of antigenic polysaccharides can also be determined such as those from *Neisseria gonorrheae, Pasteurella pestis, Shigella dysentereae*, and certain fungi such as Mycosporum and Aspergillus. An extensive list of soluble analytes determinable in the method of the invention is found in U.S. Pat. No. 3,996,345, which is incorporated herein by reference.

Apparatus Designs

A number of designs for the apparatus comprising the membrane can be used for illustration. The membrane sheet may be of any shape and of almost any size which may conveniently be handled. In a preferred embodiment, a "small" size may be used so that the sheet is suitable for being held in the hand of a user without tearing or breaking, and is generally limited to about the size of an adult human hand, though size per se is not critical. The sheet may be, and preferably is, mounted in a suitable holder provided with means for applying the sample and any necessary reagents to the sheet.

Figure 2:
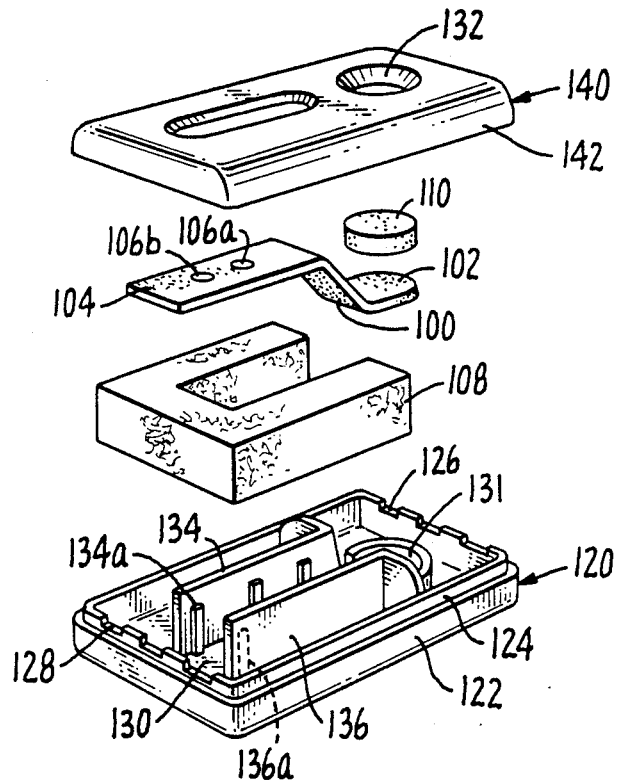
FIG. 2 is an exploded perspective view of the holder of FIG. 1 showing the components thereof and the relationship of the membrane and absorbent components contained herein.
Figure 3:
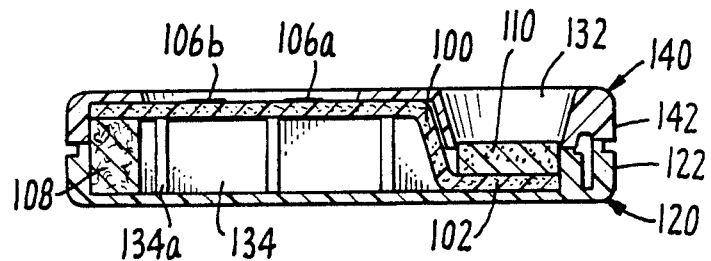
FIG. 3 is a side cross-sectional view of the apparatus of FIG. 1, take along lines 3—3 of FIG. 1 in the direction of the arrows.
Figure 4:
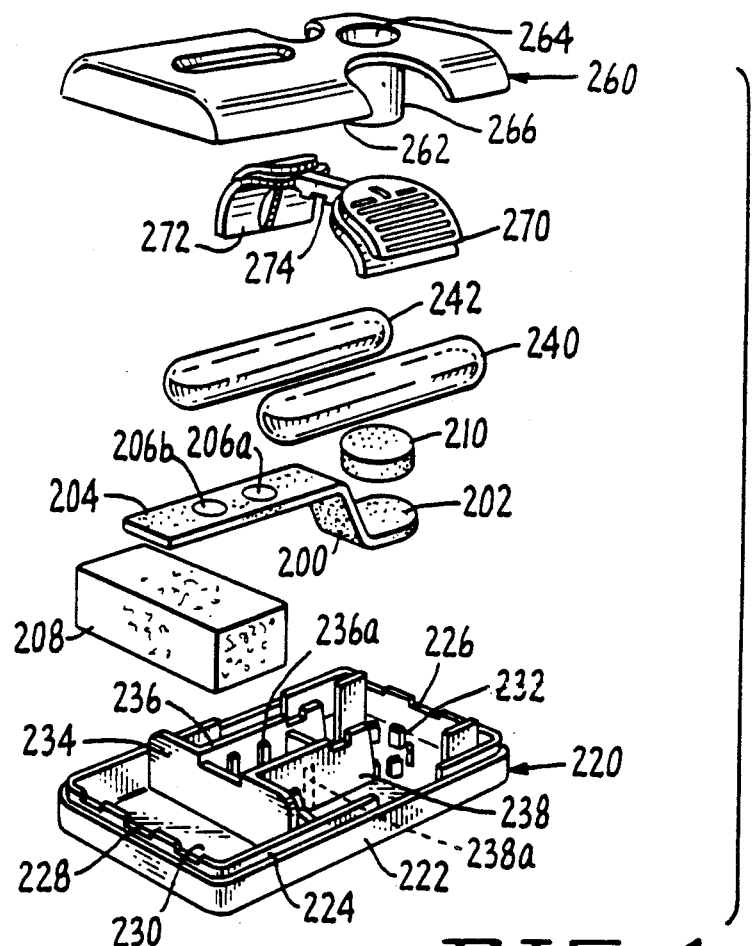
FIG. 4 is an exploded view of another preferred embodiment of the apparatus of this invention which includes reagents as well as the membrane and absorbent body.
Figure 5:
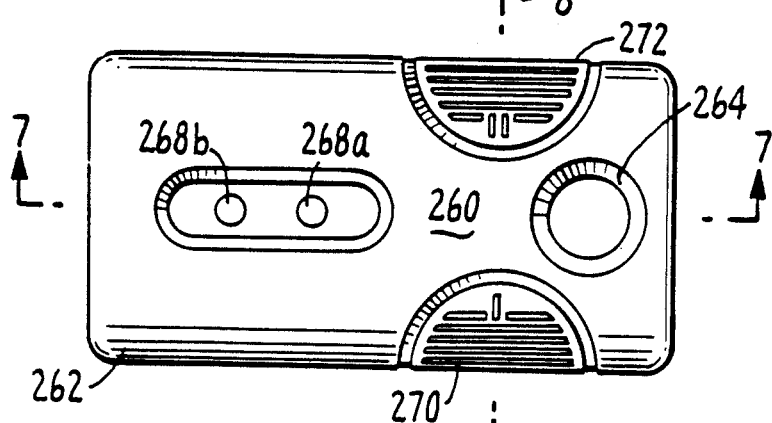
FIG. 5 is a top plan view of the apparatus of FIG. 4.
Figure 6:
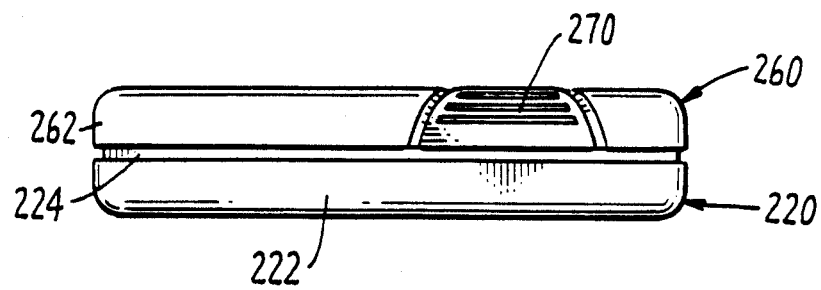
FIG. 6 is a side elevational view of the apparatus of FIG. 5.
Figure 7:
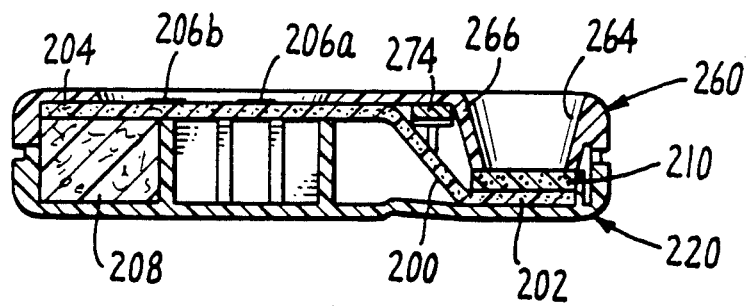
FIG. 7 is a side cross-sectional view of the apparatus of FIG. 5 taken along lines 7—7 of FIG. 5 in the direction of the arrows.
Figure 8:
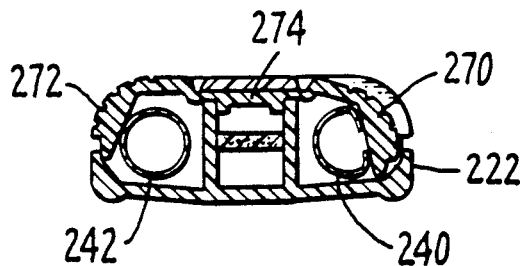
FIG. 8 is a transverse cross-sectional view of the apparatus of FIG. 5 taken along lines 8—8 of FIG. 8 in the direction of the arrows showing the breaking mechanism of the invention.

In one illustrative design, as shown in FIGS. 1-3, the lateral flow, non-bibulous membrane 100 is an elongate strip. The membrane, has an application zone 102 which is adapted to receive a liquid sample. In the illustrated apparatus there is a plurality of indicator zones 106a and 106b. At least one of such indicator zones contains the complementary member of a specific binding pair where the other member is the analyte of interest or derivative thereof, i.e., a substance which binds specifically to the analyte, e.g., an antibody-antigen. In the apparatus of FIGS. 1–3, there is also provided an absorption zone 104 which is adapted to absorb liquid flowing through the membrane from the sampling zone.

The absorption zone 104 may be of sufficient capacity to permit the required flow from the sample zone through the indicator zone(s) to be retained in the membrane. Alternatively, an absorbent body 108 which may be a pad of cellulose fibers, a cellulose sponge, or any other high-capacity hydrophilic material capable of absorbing liquid may be provided.

In the particular apparatus shown, pad or disc 110 may be used as a source of supplementary reagent. The disc may also be a non-bibulous membrane or may be a liquid absorbent, such as filter paper. For example, in an ELISA assay, disc 110 may contain enzyme-labeled antibody, which dissolves in the sample and couples with an analyte antigen. The complex is then retained in the indicator zone by additional antibody capable of binding the analyte-enzyme labelled complex which is formed.

The invention method is conducted using the apparatus of FIGS. 1–3 by introducing a liquid sample in the application zone 102. The liquid flows laterally without retention through the indicator zone 106a and 106b and into the absorption zone 104 and/or an adsorptive pad 108. Unbound species are washed from the indicator zone, if necessary, or desirable, to make reading easier. A developer or other reagent is added, if required, to develop a signal which can be detected visually, instrumentally or otherwise. The signal is relatable to the amount of the analyte. Additional steps and variations in the order of carrying out of the steps will depend upon the particular binding pair under consideration, the particular label or marker, etc., as required or desired depending on the specific mode of developing the detectable signal. In some instances, only two steps are required. For example, in one embodiment, whole blood is simply introduced to the sample application zone, unbound or unentrapped cells are washed through the indicator zone, and red blood cell color is sufficient to permit direct visual reading of the assay.

Multiple analytes in a single sample can be determined with a single apparatus by providing multiple indicator zones so that each indicator binds only one analyte.

Referring again to FIGS. 1–3, a marketable kit is shown. The kit includes, in addition to the lateral flow non-bibulous membrane 100, a base 120 which has a surrounding lip 122 forming a bottom reservoir when the kit is in use. A flange 124 extends upwardly from the lip and permits easy attachment to the top which will be described. Notches 126 at one end and 128 at the other end provide for alignment of the top and attachment of the top to the base. Inside the bottom reservoir 130 the base structure forms a support 131 for the application zone 102 of the membrane 100 and walls 134 and 136 which include a solid support or plurality of supporting columns 134a and 136a respectively on the walls which serve to support the edges of the membrane 100 in the indicator zone(s) 106 thereof. The reservoir and walls are so constructed and configured as to receive inside the reservoir the absorbent body 108 which, in the illustrated example, is a rather large U-shaped body to provide ample excess capacity in the event the operator uses excess wash, developer or other reagent solutions.

The disc 110 in addition to or instead of carrying a reagent, can act as a filter for the application zone 102 of the membrane 100 removing large particles from the sample. The disc is, however, optional. The liquid sample is introduced to the pad 110 or directly to the zone 102 by a pipette, dropper or other device.

The wash or buffer solutions and the reagents may be introduced through the pad 110 or directly to and through the application zone 102 to and through the indicator zone(s) 106. The analyte of interest, if present, is bound specifically to the membrane in one or more of the indicator zones. The wash or buffer solutions and, if used, the other reagent solutions, may also be introduced directly into the indicator area.

The top or cover 140 is constructed and adapted to fit snugly with the base 120 and includes a flange 142 which fits in close engagement with the flange 124 on the base 120. The top forms and defines an opening therethrough in the form of a well 132 which may, as shown, have chamfered or beveled sides, or may be in any shape or size or configuration of convenience. The well 132 provides access to the disc 110 for introducing sample and wash and reagents. One or more "indicator" apertures 146 e.g., 146a and 146b are also formed and defined by the top 140 permitting viewing of the "indicator" zone(s) on the membrane. These apertures may be formed of or covered with thin, clear or translucent coverings, if desired, it being necessary only that one be able to see or otherwise "read", i.e., detect, the color, radioactivity or fluorescence, or other signal, in the indicator zone. The apertures, or other indicator covering structures, may be in special shapes such as a "plus" sign, a "minus" sign, a circle, or in any other configuration to provide access to the indicator zone. The shape of the indicator access is simply a convenience and not of operational significance.

FIGS. 4–8 show a self-contained kit, i.e., a kit which does not require additional reagents or equipment. The critical membrane 200 is shown as an elongate strip, which has an application zone 202, a flow-through or absorbent zone 204 which accepts liquid laterally traversing the membrane through the "indicator" zone or a plurality of indicator zones 206, e.g., 206a and 206b. At least one of such indicator zones has bound therein a member of a specific binding complex comprising the analyte of interest and substrate which binds to analyte. An absorbent body 208 which is of a high-capacity hydrophilic material capable of absorbing the liquid is also shown. Disc 210 functions as described respecting pad 110.

The kit includes, in addition to the non-bibulous capillary flow membrane, pad and absorber described, a base 220 which has a surrounding lip 222 forming a bottom reservoir when the kit is in use. A flange 224 extends upwardly from the lip and permits easy attachment to the top which will be described. Notches 226 at one end and 228 at the other end provide for alignment of the top and attachment of the top to the base. Inside the bottom reservoir 230 the base structure forms a support 232 for the sample application zone 202 of the non-bibulous lateral flow membrane 200 and walls 234, 236, and 238 which include a plurality of supporting columns 236a and 238a respectively on the walls which serve to support the edges of the membrane 200 in the indicator zone(s) 206 thereof. The reservoir and walls are so constructed and configured as to receive inside the reservoir the absorbent body 208 which, in the illustrated example, is an absorbent body of sufficient size and shape and composition to absorb all, or substantially all of the liquids which would be used in a normal assay. The absorbent body may be of any moisture absorbent material, cellulosic fibers, fibers or particles of cellulose esters, etc. The walls 236 and 238 and the bottom 220 generally define a space for receiving two vials 240 and 242 which are of glass, polymer or other crushable or openable material. An inexpensive polymeric "vial" may be formed of any suitably inert polymeric membrane, e.g., polyethylene, polyvinyl chloride, polycarbonate, etc., of the desired size and shape having a weakened or thin area in a portion adjacent the sample zone which will rupture upon the application of pressure. A simple glass vial may, of course, be used. In this example, and this is but one illustrative example, the vial 240 contains a wash solution and the vial 242 contains a buffer solution.

The top or cover 260 is constructed and adapted to fit snugly with the bottom 220 and includes a flange 262 which fits in close engagement with the flange 224 on the bottom 220. The top forms and defines an opening therethrough in the form of a well 264 which may, as shown, have chamfered or beveled sides, or may be in any shape or size or configuration of convenience and, in this embodiment, includes surrounding skirt 266 which directs the liquid to the sample receiving pad. The well provides access to the pad 210 for introducing sample and wash and reagents to the non-bibulous capillary flow membrane 200 for carrying out the assay. One or more "indicator" apertures 268 are also formed and defined by the top 260 permitting viewing of the "indicator" zone(s) on the non-bibulous capillary flow membrane. These apertures 268 may be formed of or covered with, thin, specially formed, clear or translucent coverings, or be openings, it being necessary only that one be able to see or otherwise detect the color.

In this example, a pair of crusher buttons 270 and 272 joined by a flexible strip 274 are positioned on the sides of the top and are moveable downwardly by application of force by the user, e.g., by pressing the button. Each of the buttons is so constructed, configured and positioned that such downward movement, as viewed in the figure, will cause a portion of the button to engage one of the vials and crush, rupture or otherwise open the vial. While this is a convenient mechanism, it is not necessary to the invention that the precise mechanism be as described in the example. For example, the buttons may be independent of each other, there may be three or more vials and three or more buttons, etc. or other breaking and/or opening mechanisms may be used. The kit of FIGS. 4-8 is a preferred but only illustrative embodiment.

Figure 9:
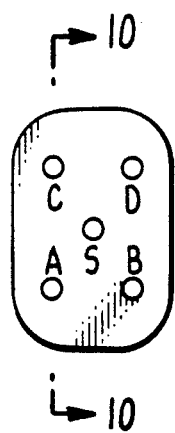
FIG. 9 is a plan view of an alternative, simplified form of an apparatus suitable for use in this invention, especially for blood typing.

A simple but very effective form of the invention apparatus is shown in FIG. 9. This apparatus comprises a sheet of the isotropic lateral flow, non-bibulous, membrane having, near the center thereof, an application zone S which is adapted, constructed and treated as necessary to receive and absorb for example, a cell-bearing liquid sample, e.g., blood. At least one indicator zone A and, in this embodiment, a plurality of indicator zones A, B, C and D are provided equidistantly spaced (in this illustration) from the sample application zone S. In this illustration there is additional membrane beyond each indicator zone as an "absorbent zone" to encourage flow of sample. The geometry is, of course, arbitrary; the requirements being that there be an application zone capable of receiving from an external source an aqueous liquid, optionally but preferably an absorption zone capable of permitting additional flow of liquid in the membrane, and intermediate to, and spaced from, each of the application and absorption zones, at least one indicator zone; the indicator zone being different from the remainder of the membrane in that to it is affixed one member of a binding pair, e.g., an antibody or a receptor, or an antigen.

Figure 10:
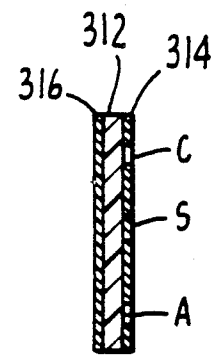
FIG. 10 is a cross-sectional view of the apparatus of FIG. 9.

As shown in FIG. 10, a substantially liquid impervious film or layer 314 may be bonded to one side of the membrane 312, there being formed a sample receiving aperture S and one or more apertures at A and C, for example for viewing indicator zones. Additionally, another liquid impervious film or layer 316 may be bonded to the other side of the membrane to form a sandwich. The liquid impervious layers are, e.g., polyethylene or other polymer film, or paper which has been coated or treated, e.g., with wax or a hydrophobic polymer such as silicone.

In one manner of conducting the method with this illustrated apparatus, sample is applied to S and allowed to flow through A-D to which is affixed a member of a binding pair. Sufficient time of incubation (30 sec-several minutes) is used in order to permit the analyte to react with a binding partner affixed in one or more indicator zone A-D. This is followed by washing conveniently by applying wash solution to S, and then by detection of bound analyte in A-D.

Illustrative Applications of the Invention Apparatus

Analysis of Blood Samples

One major application of the invention apparatus is in blood typing and characterization. In the assessment of whole blood, red blood cells can be used as a detection reagent, whether directly bound by their surface antigens to the binding pair member in the indicator zone or entrapped by a complex formed between members of a different binding pair in said zone. Both soluble and particle-borne analytes are capable of forming such complexes.

Blood Typing and Characterization

Thus, for example, the invention apparatus and methods are useful for determining the blood grouping of erythrocytes (A, B, 0, Rh) or cell typing with leucocytes or platelets (HLA or Pl$^{41}$).

By way of background, cells found in mammalian blood are, principally, erythrocytes (red blood cells or red blood cells), thrombocytes (platelets), granulocytes, monocytes, T lymphocytes and B lymphocytes (leucocytes). Specific binding pair immunochemistry of erythrocytes is important in whole blood transfusions in which the ABO and Rh blood group matching is required. Matching of antigens associated with other blood cell types is also important in transplantation and in individual identification—e.g., HLA typing.

The *TECHNICAL MANUAL of the American Association of Blood Banks*, American Association of Blood Banks, Arlington, Virginia, describes the most widely used nomenclature. The most common blood groups are the ABO and the Rh blood group systems. A and B refer to antigens present on red blood cells, type O does not contain these antigens. Rh positive blood cells contain the "Rh" or "D" antigen. The reality is somewhat more complex, however as a first approximation, the following immunological binding relationships are defined.

ABO Blood Grouping*

| Cell Reaction with Antibodies to Blood Group Antigens | | Reaction of Serum Tested Against Blood Group Cells | | | ABO Group |
|---|---|---|---|---|---|
| Anti-A | Anti-B | A Cells | B Cells | O Cells | |
| − | − | + | + | − | O |
| + | − | − | + | − | A |
| − | + | + | − | − | B |
| + | + | − | − | − | AB |

*Taken from the Technical Manual of the American Association of Blood Banks.

Rh Blood Grouping

| Reaction with Rh Blood Group Antigen D | Rh Group |
|---|---|
| + | Positive |
| − | Negative |

Reference is made to the aforesaid Technical Manual and to more comprehensive works for a more complete description of blood groupings and related nomenclature. Specific binding ABO dipsticks are disclosed by Plapp, F. V., et al, *The Lancelet*, June 28, 1986, pp. 1465–1466.

Platelet antigens, $Pl^{A1}$ and $Pl^{A2}$, $Ko^a$ and $Ko^b$, and $Pl^{E1}$ and $Pl^{E2}$, and other less common platelet antigens naturally occur on the surface of platelets in humans at a greater or lesser frequency. For example, $Pl^{A1}$, which is associated with the control of bleeding episodes, occurs in about 97% of the population and $Pl^{A2}$ occurs in about 27% of the population.

Human Lymphocyte Antigens (HLA) and other $Pl^A$ antigens occur on the surface of platelets. $Pl^A$ antigens are specific to platelets, however, while HLA are found on all nucleated cells in the body, those of solid tissue and most of the circulating blood cells, except red blood cells. The major human histocompatibility complex (MHC) is a cluster of genes denominated HLA-A, HLA-B, HLA-C, HLA-D and HLA-DR which produce antigens. HLA-A, HLA-B and HLA-C antigens constitute the major transplantation antigens. HLA-D and HLA-DR are believed to be involved in immune responsiveness.

HLA typing is fundamental to paternity determinations, therapy involving blood components, organ transplant and transfusion compatibility determinations, and in other medical and scientific studies.

In blood therapy, a high percentage of patients receiving repeated transfusion of random-donor platelet transfusions become refractory to further random-donor platelet transfusions, but single donor HLA-matched platelets can be of benefit in treating many of these refractory patients. HLA-A, HLA-B, and HLA-C antigens are considerably more important in selecting single-donor platelets than ABO antigens which, at most, are weakly expressed on platelets and HLA-D and -DR which are not present on the platelet surface. Perfect single-donor HLA-platelet matching is, at best, an arduous process, requiring a very large donor pool and a great many matching tests. It would, therefore, be an advance of great importance that the matching tests be carried out quickly and inexpensively.

The standard technique used to detect HLA-A, -B, -C, -D, -DR and -DQ antigens is the microlymphocytotoxicity test. The HLA-D system is determined by cellular events in mixed lymphocyte culture (MLC) tests. Primed lymphocyte typing (PLT) and Cell-Mediated Lympholysis (CML) tests are also used in HLA antigen testing. These methods and other current methods for HLA typing require sophisticated and expensive equipment and highly trained technicians; see "HLA Techniques for Blood Bankers and Technical Manual of the American Association of Blood Banks", (1984), American Association of Blood Banks, Arlington, VA, USA.

Other cytotoxicity based HLA typing methods have also been reported; see, e.g., Grumet, et al, U.S. Pat. No. 4,471,056; Terasaki, et al, U.S. Pat. No. 4,599,315; and U.S. Pat. No. 4,324,026.

Specific binding reaction HLA assays have also been described, DeFreitas, U.S. Pat. No. 4,492,760 (assay for HLA-D typing using monocytes which had been contacted with a particular antigen and then incubated with antigen-specific T lymphocytes or antigen-specific T cell hybridomas) Engleman, et al, U.S. Pat. 4,634,666 (immuno-fluorescent assay for HLA antigens using monoclonal antibodies), Old, et al, U.S. Pat. No. 4,650,756 (monoclonal antibodies which bind to HLA); Eisinger, R. W. and R. A. Eatz, Program and Abstract First Annual ASM Conference on Biotechnology, 1986.

Platelet antibody assays generally have been described by Schiffer, C. A., in "A Seminar in Antigens in Blood Cells and Body Fluids", Bell, C. A., ed., Washington, D.C. American Association of Blood Banks; 1980:189–208) and Brand, A., et al, (*Blood* (1978) 781–788) and many others.

A summary of some of the available non-red blood cell surface markers is summarized in the table below:

TABLE IV

| | Differentiation of Lymphocytes | | |
|---|---|---|---|
| Marker | T Cell | B Cell | Macrophage |
| Specific Surface Antigens | OKT, Leu | HBLA | OKM1 |
| Antigen Binding Receptor | V Region | Ig | — |
| Receptors for: | | | |
| sRBC (E-rosette) | + | − | − |
| IgG Fc (EA-rosette) | + | + | + |
| IgM Fc (EA-rosette) | + | − | − |
| C3b (EAC rosette) | − | + | + |
| Measles Virus | + | − | − |
| Epstein Barr Virus | − | + | + |
| HLA-A,B,C Antigens | + | + | + |
| HLA-D/Dr Antigens | +/− | + | + |

Reference: Herscowitz, "Immunophysiology: Cell Function and Cellular Interactions in Antibody Formation" in Immunology III edited by J. A. Bellanti, W. B. Saunders Co., Philadelphia, 1985.

As further described below, the invention method is particularly useful in assessing the presence or absence of these cell surface markers in blood. Antibodies to the cell surface marker of interest are placed in an indicator zone and a sample of blood to be tested is placed in the application zone in sufficient volume to flow past the indicator zone(s). Multiple indicator zones, each having affixed antibody for a different cell surface marker, may be used. A radial arrangement, such as that of FIG. 9 may be convenient. All of the indicator zones will appear red. After a suitable incubation period, usually less than a minute, wash solution is then flowed past the indicator zone(s), most conveniently by supplying the wash solution to the application zone in sufficient amount to wash away all unbound or unentrapped red blood cells. A control "blank" zone equidistant with the other indicator zones from the application zone is useful in verifying the correct quantity of wash; this zone will appear clear when sufficient wash is added. The results can then be read: indicator zones which have affixed antibodies to cell surface markers present in the sample will appear red; those with antibodies to markers not present will be clear. If the cell surface markers are on the red blood cells, the red blood cells will be directly bound to the fixed antibody in the zone; if the markers are on platelets or leucocytes, the red blood cells will be entrapped in the complex formed by these cells with the fixed antibody.

Determination of Soluble Blood Components

It has been found that complexes formed between fixed antibody (or other binding partner) and soluble blood components are also capable of entrapping red blood cells to generate a red color in the reaction zone. Thus, soluble materials in the blood are assessable in an analogous way. For example, proteins and nucleic acid associated with infection are capable of antibody recognition or recognition by other binding partners. Other blood components such as antibodies or lipoproteins can also be detected.

For example, during the initial stages of Hepatitis B Virus infection, the Hepatitis B surface Antigen (HBsAg) is detected in the serum, followed by a measurable amount of Hepatitis B envelope Antigen (HBeAg) and antibody to Hepatitis B core Antigen (anti-HBcAg) titer during the acute stage of the disease. Production of anti-HBeAg and anti-HBsAg occur later. All of these are detectable by binding assay protocols, as are indications of Herpes Simplex I and II, HIV and cytomegalovirus infections.

Other important soluble blood components include lipoproteins which are conjugated proteins in which the prosthetic groups are lipids. These are also found in cell cytoplasm. Assay of lipoproteins is of interest, because there is a direct correlation between the blood level of lipoproteins, especially low density lipoproteins, and the risk of cardiovascular disease, such as atherosclerosis. Apolipoprotein A-1 and Apolipoprotein B in serum are key indicators and are considered to play a key role in the progress and management of cardiovascular diseases.

For detection of soluble components in whole blood, in the typical protocol, as for cell surface markers, whole blood is used as the sample, and a material specifically reactive with the soluble analyte is fixed in an indicator zone. Multiple indicator zones can be used, each with a specifically reactive complementary member for binding to the soluble analyte.

For example, to test for lipoprotein, a whole blood sample of about 4-5 drops is applied to the application zone of the apparatus of FIG. 9 wherein the indicator zones A, B, C or D contain antibody to the lipoprotein(s) or lipoprotein derived or related component(s) to be determined. Sufficient volume is applied to allow for lateral migration through the membrane through the indicator zones. A brief incubation of from a few (e.g., 15) seconds to several (e.g., 30) minutes, typically between one and two minutes at room temperature, permits the binding of the lipoprotein to the member of the specific binding pair affixed to the indicator zone. For example, one might affix anti-apolipoprotein A-1 in a first zone, anti-apolipoprotein B in the second, anti-apolipoprotein E in a third, etc. After sample addition, a lattice network is formed between the affixed antibodies and the lipoprotein which entraps the erythrocytes from the blood. Thus, when wash is added to the application zone and flows laterally through the indicator zones, those containing bound analyte retain the red blood cells and appear red. In those which do not, the red blood cells will be washed away and these indicator zones will appear clear.

Use of Added Detectable Particles

It will be evident that while assay of whole blood furnishes a convenient source of visible particles, non-blood samples could also be used with the addition of visible particles. For example, red blood cells or colored latex beads or the like could be used to supplement a serum sample, spinal fluid, or urine sample. The particles can be added along with sample, or subsequent thereto.

For instance, for detection and titration of antibody to viral components in serum, viral antigen components or the denatured virus itself can be affixed to an indicator zone. While whole blood could be used, as described above, in the alternative, the serum can be tested directly when supplemented with red blood cells or other colored particles. Conversely, to detect a viral or bacterial antigen, a monoclonal or polyclonal antibody directed to the antigen is fixed to the indicator zone. As before, the sample modified to contain detectable particles is applied at the application zone and flows laterally through the indicator zone. In an alternative, the particles can be added subsequent to sample. In another alternative, the particles could be impregnated into the application zone during manufacture. For example, latex beads could be lyophilized in place in the application zone. The complex resulting in the indicator zone provides a lattice network which entraps the particles, giving a positive reaction, e.g., a visible color at the indicator zone rather than a clear zone.

In general, then, serum, urine, spinal fluid, plasma, or other body fluid, or liquid from other sources, such as manufacturing lots in the pharmaceutical, food or cosmetic industry, effluents from industrial processes, or any liquid suspected of containing a specific analyte can be used as sample. The analyte is detected in the invention method by providing a fixed binding pair member, capable of binding analyte or derivative thereof, in an indicator zone, and by providing a suspension of detectable particles along with the sample, or subsequent to the passage of sample through the indicator zone. The detection is by appearance of the detectable particles, after washing, in the indicator zone.

Applications in general include monitoring antigens and antibodies during stages of infection, and for general diagnosis and monitoring of therapy. Hormones, enzymes, other blood proteins, or tumor antigens shed into the bloodstream or other body fluids following chemotherapy or radiation therapy may also be monitored.

Detection Using Non-Particulate Label

While detectable particulate entrapment, especially visible particle entrapment, is a convenient method, other specific binding assays are adaptable to the method and apparatus of the invention, as set forth above. For example, the standard hCG ELISA test for pregnancy can be adapted to this method either with separate or self-contained reagents.

Generally, for the hCG assay, a urine sample is applied to the application zone and allowed to flow through an indicator zone containing anti-hCG antibodies. After washing, a second, labeled anti-hCG is then applied to the indicator zone either directly or by flow from the application zone, and, if needed, followed by developing reagents. If the label is an enzyme, the developing reagents will include the enzyme substrate. Alternatively, the urine sample can be treated first with labeled murine anti-hCG and the mixture flowed laterally through an indicator zone to which is fixed a monoclonal anti-hCG Ig preparation which binds to a different epitope. A variety of protocols can be used.

The reagents can be added independently as in the apparatus of FIGS. 1-3, or they can be self contained, as in that of 4-8. In the latter case, for example, the indicator zone may contain fixed anti-hCG; a vial included in the apparatus may contain enzyme-labeled anti-hCG.

"Reverse" Assay Protocols

In addition to the standard method of supplying sample to the application zone, the protocol can, of course, be reversed by affixing the analyte from a sample into an indicator zone and supplying detecting reagent by lateral flow from the application zone. For example, the presence of a specific antibody or antigen in serum can be detected by affixing the serum sample to the indicator zone, followed by addition to the application zone of a labeled form of the complementary antigen or antibody, respectively. In this manner, multiple samples can be assayed in the apparatus of FIG. 9-10, or of other design, by utilization of the multiplicity of indicator zones.

By way of illustration, four different serum samples to be tested for the presence of herpes virus protein are affixed individually to zones A-D by drying the samples applied to these indicator zones. The application zone is then employed to effect the flow of a reagent solution containing labeled anti-hepatitis antibodies through the membrane and past the indicator zones. Incubation time is allowed to permit any viral protein in the samples to bind to antibody, and a wash solution is then applied to the application zone to wash away antibody not bound to the indicator zones. If the label is an enzyme, this is followed by a detection reagent such as a substrate mixture. Alternatively, non-labeled antibodies can be used as the initial reagent, followed by addition of, for example, colored particles as described above, or a labeled antibody reactive either with the viral antigen or with the antibody reagent. The presence of label showing viral antigen in a particular zone indicates the presence of viral antigen in the relevant sample.

In an alternative protocol, for example, urine samples to be tested for the presence of hCG are placed individually in indicator zones A-D and dried. A reagent containing labelled anti-hCG antibody is supplied to the application zone and permitted to flow through the membrane past the various indicator zones A-D. After a suitable incubation period, a wash solution is applied at the application zone S, or in the alternative, directly to the indicator zones. The presence of label in an indicator zone, then, demonstrates the presence of hCG in the sample.

In another example, compatibility for platelet transfusion between potential donors and a recipient can be determined. Serum from the donor can be placed on multiple test units in an indicator zone and dried. A whole blood test sample from a potential donor is supplied to the application zone and permitted to laterally flow through the indicator zone. After a suitable incubation, a wash solution is applied in the application zone. A lack of signal is indicative of compatibility between the recipient and the tested donor. A positive reaction (red spot in the indicator zone) is indicative of an incompatible match due to antibodies present in the recipient's serum recognizing and binding the antigens present on the potential donor's platelets. The incompatible match results in exclusion of this donor for the recipient. Multiple donors can be screened using multiple test units.

In an alternative form, serum samples from several recipients requiring platelet transfusions could be tested against a single potential donor to determine compatibility/incompatibility. Serum from each recipient would be spotted into individual indicator zones and dried. A whole blood test sample from a potential donor could be applied at the application zone and compatibility with any of the recipients determined. This type of antibody screen assay would be applicable for platelet, red blood cell and other cell components transfusion compatibility or crossmatch testing.

Semi-Quantitative Assay

By varying the amount of specific binding pair member in a multiplicity of indicator zones on the membrane, the assay can be made semiquantitative. For example, serial dilutions of antibody can be used in zones A-D of the apparatus of FIG. 9-10, and sample to be analyzed for antigen provided to the application zone. Labeling can be by subsequent addition of, e.g., labeled Ig capable of binding to the complex, or by the use of detectable particles.

In this assay, higher concentrations of analyte are able to show detectable reactions to lower amounts (higher dilutions) of affixed binding pair member. Thus, by calibrating serial dilutions of a binding pair member preparation, affixed over a series of indicator zones, to varying concentrations of analyte, an at least semi-quantitative result can be obtained.

EXAMPLES

The following examples illustrate, but do not limit the invention.

EXAMPLE 1

Determination of Platelet Antigen Components

The illustrative apparatus of FIGS. 9 and 10 was used to determine the platelet surface antigen in blood samples. There are two major groups of glycoproteins present on the platelet cell surface; platelet-specific antigens ($Pl^{A1}$, $Pl^{A2}$, $Pl^E$, Lek, Bak, Duzo) and platelet-associated antigens (HLA-A, -B, -C antigens), which are also found on other cell types.

Referring to FIG. 9, whole blood is applied to the application zone, S, the sample components, including platelets and red blood cells, laterally flow through the membrane passing the indicator zones, each of which contains antibody specific to a platelet antigen. In zones containing antibody specific for a platelet marker present in the sample, the bound platelets form a lattice network which entraps the red blood cells in the test sample. This is evidenced as a red color in the zone following the addition of wash buffer to remove unbound cells. A clear or white zone is indicative of a lack of the relevant marker.

Pl$^{A1}$ Antigen

Extra Fine grade and Fine grade Ultra High Molecular Polyethylene porous plastic (Porex Technologies Inc., Fairburn, GA) was cut into two-inch long×0.5 inch strips. Five microliters of antibody with demonstrated specificity to the Pl$^{A1}$ antigen (Lot KRO, Blood Center of Southeastern Wisconsin) was spotted approximately one inch from the end of the porous plastic strip. The positive control for this assay consisted of spotting 5 µl of Rabbit Anti-Thrombocyte Membrane (Dako, Lot 035) onto duplicate strips. This antibody binds all platelets regardless of Pl$^{A1}$ phenotype. The strips were dried at either 37° C. or 25° C. for 15 minutes. The dried strips were stored at 25° C. with desiccant capsules (Dricap, Multiform Desiccants, Inc.).

Prior to performance of the assay, absorbent pads (Schleicher and Schuell, #A300) were attached to one end of the porous plastic strip. Platelets were previously typed for Pl$^{A1}$ antigen by the immunofluorescence procedure (St. Louis. American Red Cross). Blood samples were collected in ethylenediamine tetraacetic acid (EDTA) anticoagulant. Four to five drops (100–125 µl) of whole blood were added to the sample application end of the porous plastic strip. This ensured a sufficient volume of blood to flow laterally past the antibody spotted region. Following a three minute incubation at 25° C., 16–20 drops of wash reagent were added to the sample application end. This caused the unbound cells to flow from the antibody spotted region to the absorbent pad area.

A positive reaction was characterized by a red dot at the site of antibody application. This results when the porous plastic affixed antibody (Anti-Pl$^{A1}$) antibodies recognize the Pl$^{A1}$ antigen present on the platelet cell surface and bind the platelets. This subsequently forms a lattice which entraps the red blood cells in the test sample. A negative reaction is identified as a clear or white region at the antibody application site.

Blood samples from three donors identified as being Pl$^{A1}$ positive by immunofluorescence produced a positive reaction with an Anti-Pl$^{A1}$ serum (Lot KRO); negative reactions were obtained from two Pl$^{A1}$ negative donors. (A positive control in the assay used Rabbit Anti-Thrombocyte (Dako Lot 015) as a binding antibody in the reading zone; it binds thrombocytes regardless of Pl$^{A1}$ phenotyping. Blood samples from all five donors tested produced positive reactions.)

Results

| Donor ID | Anti-Pl$^{A1}$ status* | Positive Control | RBC Lateral Flow |
|---|---|---|---|
| ABO#211 | Negative | Positive | Negative |
| ABO#132 | Positive | Positive | Positive |
| ABO#131 | Positive | Positive | Positive |
| ABO#130 | Negative | Positive | Negative |
| ABO#129 | Positive | Positive | Positive |

*As determined by immunofluorescence testing, St. Louis Chapter American Red Cross.

EXAMPLE 2

ABO Rh Grouping

Fine grade Ultra High Molecular Weight Polyethylene porous plastic (Porex Technologies, Inc., Fairburn, GA) was cut into 1.5 inch long×1.5 inch blocks. The block was assembled between two polystyrene pieces slightly larger than the porous plastic block. Five wells or windows were punched out of the top polystyrene piece at a distance of approximately 0.25 inches from the center of the porous plastic block. Four microliters of either monoclonal Anti-Blood Group A (Ortho Diagnostics, Lot 109D), monoclonal Anti-Blood Group B (Ortho Diagnostics, Lot BBB 506A) or Anti-Blood Group Rh (Ortho Diagnostics, Lot DN 298A) were spotted into individual wells. The positive control for this assay consisted of spotting 4 µl of Rabbit Anti-Erythrocyte Membrane (Dako, Lot 015) into a fourth well. This antibody binds all erythrocytes regardless of ABO Rh blood type. A fifth well serves as the negative control well and is not spotted with any antibody, but serves to demonstrate the lack of nonspecific reactions as well as the complete removal of unbound red blood cells from the test area. The spotted units were dried at 37° C. for 30 minutes. The dried units were stored at 25° C. with desiccant capsules (Dricap, Multiform Desiccants, Inc.).

Blood samples were collected in EDTA acid citrate dextrose, or ACD; citrate phosphate dextrose, or CPD; citrate phosphate dextrose adenine, or CPDA-1; or Adsol, a brand name of Baxter-Travenol, Chicago, Illinois; or heparin anticoagulants. Four drops (100–125 ul) of whole blood were added to the center sample application well. This ensured a sufficient volume of blood to flow laterally past the antibody spotted regions. Following a thirty second incubation at 25° C., 16–20 drops (approximately 0.5–0.6 ml) of wash reagent were added to the center sample application well. This caused the unbound cells to flow from the antibody-spotted (indicator) region to the remaining (absorbent) region of the porous plastic block.

A positive reaction was characterized by a red dot at the site of antibody application. This results when the antibody affixed to the porous plastic recognizes the appropriate erythrocyte cell surface antigen and binds the red blood cells. A negative reaction is identified as a clear or white region at the antibody application site.

The following results were obtained:

| Blood Group* | Total Samples Tested | Number Correctly Identified by RBC Lateral Flow |
|---|---|---|
| A | 65 | 65 |
| A$_x$ | 7 | 7 |
| B | 47 | 47 |
| O | 88 | 88 |
| AB | 31 | 31 |
| Rh Positive | 141 | 141 |
| Rh Negative | 98 | 98 |
| D$^u$ Positive | 4 | 4 |

*Determined by Routine Tube Testing hemagglutination procedures

EXAMPLE 3

ABO Reverse Grouping Immunoassay

The serum of type O blood contains anti-A and anti-B immunoglobulins, that of type B blood contains anti-A; that of type A blood, anti-B. Thus blood can also be typed by detecting these antibodies in serum. The test sera are spotted into indicator zones and fixed and assayed by applying whole blood of known type to the application zone.

Extra Fine grade Ultra High Molecular Weight Polyethylene porous plastic (Porex Technologies, Fairburn, Ga) was cut into two-inch long×0.5 inch strips. Five ul of serum from a Blood Group A donor (MH), a Blood Group B donor (RWE), a Blood Group O donor (ABO #31) and a Blood Group AB donor (Serologicals #44) were spotted approximately one inch from the center on duplicate porous plastic strips. The positive control for this assay consisted of spotting 5 ul of Rabbit Anti-Erythrocyte Membrane (Dako, Lot 015) at a second site on each strip. The positive control antibody binds all red blood cells regardless of blood grouping.

The strips were dried at either 37° C. or 25° C. for 15 minutes The dried strips were stored at 25° C. with desiccant capsules (Dricap Co.).

Prior to performance of the assay, absorbent pads (Schleicher and Schuell, #A300) were attached to both ends of the porous plastic strip. Red blood cells which had been previously typed using routine tube testing hemagglutination procedures were collected in ethylene-diamine tetraacetic acid (EDTA) anticoagulant. Four to five drops (100–125 ul) of whole blood from identified Blood Group A or Blood Group B donors were added to the center of each porous plastic strip. This ensured a sufficient volume of blood to laterally flow past the antibody spotted regions. Following a one minute incubation at 25° C., 6–8 drops of wash reagent were added to the center of the strip. This caused the unbound cells to flow from the antibody spotted region to the absorbent pad area.

A positive reaction was characterized by a red dot at the site of antibody application, e.g., red color will appear for blood type O when tested with A and B red blood cells; for blood type B with group A red blood cells; and for blood type A with group B red blood cells. Type AB serum will produce clear (negative) reactions with both group A and group B red blood cells.

The results are as follows:

| Donor ID | RTT Grouping* | Positive Control | RBC Lateral Flow | |
|---|---|---|---|---|
| | | | A Cells | B Cells |
| MH | Group A | Positive | Negative | Positive |
| RWE | Group B | Positive | Positive | Negative |
| ABO#31 | Group O | Positive | Positive | Positive |
| Sero.#44 | Group AB | Positive | Negative | Negative |

*As determined by standard Routine Tube Testing Procedures.

EXAMPLE 4

A Red Blood Cell Typing (Unexpected Red Blood Cell Antibody Screen) Immunoassay

Extra Fine grade Ultra High Molecular Weight Polyethylene porous plastic (Porex Technologies Inc., Fairburn, GA) was cut into two-inch long×0.5 inch strips. Five microliters of ANTI-C (Ortho Diagnostics, Lot CS 157A) were spotted approximately one inch from the center of the porous plastic strip. The positive control for this assay consisted of spotting 5 ul of Rabbit Anti-Erythrocyte Membrane (Dako, Lot 015) at a second site on the strip. The positive control antibody binds all red blood cells regardless of blood grouping. The strips were dried at either 37° C. or 25° C. for 15 minutes. The dried strips were stored at 25° C. with desiccant capsules (Dricap Co.).

Prior to performance of the assay, absorbent pads (Schleicher and Schuell, #A300) were attached to both ends of the porous plastic strip. Red blood cells were previously typed using Routine Tube Testing hemagglutination procedures (University of California, San Diego Medical Center). Blood samples were obtained from collection unit segments containing CPD anticoagulant. Four to five drops (100–125 ul) of whole blood from a donor were added to the center of the porous plastic strip. This ensured a sufficient volume of blood to laterally flow past the antibody spotted regions. Following a 1.5 minute incubation at 25° C., 16–20 drops of wash reagent were added to the center of the strip. This caused the unbound cells to flow from the antibody spotted region to the absorbent pad area.

A positive reaction was characterized by a red dot at the site of antibody application. This results when the antibody affixed to the porous plastic recognizes the specific red blood cell antigen present on the cell surface and binds the red blood cell. A negative reaction is identified as a clear or white region at the antibody application site.

Results

| Donor ID | RTT Grouping* | Positive Control | RBC Lateral Flow |
|---|---|---|---|
| KC | C positive | Positive | Positive |
| PB | C negative | Positive | Negative |

*As determined by standard Routine Tube Testing procedures, UCSD Medical Center.

EXAMPLE 5

Tissue Typing Immunoassay

A. Extra Fine grade and Fine grade Ultra High Molecular Weight Polyethylene porous plastic (Porex Technologies Inc., Fairburn, GA) was cut into two-inch long×0.5 inch strips. Five microliters of Rabbit ANTI-Thrombocyte Membrane (Dako, Lot 035) were spotted approximately one inch from the center of the porous plastic strip. The anti-thrombocyte is specific to binding platelets and thrombocytes. The positive control for this assay consisted of spotting 5 ul of Rabbit Anti-Erythrocyte Membrane (Dako, Lot 015) at a second site on the strip. The positive control antibody binds erythrocytes, but does not bind to platelets. A third region of each strip was designated as the Negative control. This area was not spotted with an antibody, rather it served to demonstrate appropriate removal of unbound red blood cells from the strip and lack of non-specific reactions. The strips were dried at 37° C. for 15 The dried strips were stored at 25° C. with desiccant capsules (Dricap Co.).

Prior to performance of the assay, absorbent pads (Schleicher and Schuell, #A300) were attached to both ends of the porous plastic strip. Blood samples from two group O donors were obtained in EDTA anticoagulant. Four to five drops (100–125 ul) of whole blood from a donor were added to the center of the porous plastic strip. This ensured a sufficient volume of blood to laterally flow past the antibody spotted regions. Following a 30 second incubation at 25° C., 4–6 drops of wash reagent were added to the center of the strip. This caused the unbound cells to flow from the antibody spotted region to the absorbent pad area.

Assay specificity was tested by preparation of Platelet Rich Plasma from aliquots of each test sample to remove the thrombocytes and platelets. The remaining packed red blood cells were subsequently washed three times in PBS. Four drops of each cell suspension were subsequently tested as described above.

The addition of 100 ul of the Platelet Rich Plasma to the washed red blood cell fractions was performed to demonstrate the cell specificity of the reactions. A positive reaction was characterized by a red dot at the site of antibody application. This results when the antibody affixed to the porous plastic recognizes antigens present on platelet and thrombocyte cell surfaces and binds these cells thus forming a lattice network entrapping red blood cells in the test sample. A negative reaction is identified as a clear or white region at the antibody application site.

Whole blood samples from two donors, previously typed by lymphocytotoxicity as HLA-A2, produced positive reactions; one donor who was typed HLA-A2 negative gave a negative reaction. All three donors, regardless of HLA profile, gave positive reactions with the Anti-Thrombocyte positive control. The above assay provides a simple alternative to current methods to provide platelet type evaluation to crossmatch donor/receptor in transfusions.

Results

| Donor ID | Anti-Thrombocyte | Anti-Erythrocyte | Negative Control |
|---|---|---|---|
| ABO#45(Gr.O) | Positive | Positive | Negative |
| ABO#45(Gr.O)-less PRP | Negative | Positive | Negative |
| ABO#45(Gr.O)-Add Back | Positive weak | Positive | Negative |
| ABO#208(Gr.O) | Positive | Positive | Negative |
| ABO#208(Gr.O)-less PRP | Negative | Positive | Negative |
| ABO#208(Gr.O)-Add Back | Positive weak | Positive | Negative |

B. HLA-Typing: Extra Fine grade and Fine grade Ultra High Molecular Weight Polyethylene porous plastic (Porex Technologies Inc., Fairburn, GA) was cut into two-inch long×0.5 inch strips. Five microliters of antibody with demonstrated specificity to the HLA-A2 antigen (Lots AZ-18 or ALBQ14, Plasma Services, Scottsdale, AZ) were spotted approximately one inch from the end of the porous plastic strip. The positive control for this assay consisted of spotting 5 ul of Rabbit Anti-Thrombocyte Membrane (Dako, Lot 035) which binds all platelets regardless of HLA phenotype. The strips were dried at either 37° C. or 25° C. for 15 minutes. The dried strips were stored at 25° C. with desiccant capsules (Dricap Co.).

Prior to performance of the assay, absorbent pads (Schleicher and Schuell, #A300) were attached to one end of the porous plastic strip. Platelets were previously typed for HLA-A2 antigen by the microlymphocytotoxicity procedure (University of California San Diego Medical Center). Blood samples were collected in Ethylene Diamine tetraacetic acid (EDTA) anticoagulant. Four to five drops (100–125 ul) of whole blood were added to the sample application end of the porous plastic strip. This ensured a sufficient volume of blood to flow laterally past the antibody spotted region. Following a three minute incubation at 25° C., 16–20 drops of wash reagent were added to the sample application end. This caused the unbound cells to flow from the antibody spotted region to the absorbent pad area.

A positive reaction was characterized by a red dot at the site of antibody application. This results when the antibody affixed to the porous plastic (Anti-HLA-A2) recognizes the HLA-A2 antigen present on the platelet cell surface and binds the platelets. This subsequently forms a lattice network which serves to entrap the red blood cells in the test sample. A negative reaction is identified as a clear or white region at the antibody application site.

Whole blood samples from two donors, previously typed by lymphocytotoxicity as HLA-A2, produced positive reactions; one donor who was typed HLA-A2 negative gave a negative reaction. All three donors, regardless of HLA profile, gave positive reactions with the Anti-Thrombocyte positive control. The above assay provides a simple alternative to current methods to provide platelet type evaluation to crossmatch donor/receptor in transfusions.

Results

| Donor ID | Anti-HLA-A2 status* | Positive Control | RBC Lateral Flow |
|---|---|---|---|
| JS | Negative | Positive | Negative |
| RWE | Positive | Positive | Positive |
| NA | Positive | Positive | Positive |

*As determined by microlymphocytotoxicity testing, UCSD Medical Center.

EXAMPLE 6

Detection and Quantitative Measurement of Apolipoprotein B

Fine grade Ultra High Molecular Weight Polyethylene porous plastic (Porex Technologies Inc., Fairburn, GA) was cut into 1.5 inch long×1.5 inch blocks. The block was assembled between two polystyrene pieces slightly larger than the porous plastic block. Six wells or windows were punched out of the top polystyrene piece at a distance of approximately 0.25 inches from the center of the porous plastic block. Five microliters of either Sheep Anti-Human Apolipoprotein B (Boehringer Mannheim, Lot 10688829-07) or serially diluted Sheep Anti-Human Apolipoprotein B antibody were spotted into individual wells. The positive control for this assay consisted of spotting 5 ul of Rabbit Anti-Erythrocyte Membrane (Dako, Lot 015) into a fourth well. This antibody binds all erythrocytes regardless of ABO Rh blood type. A Negative Control well is not spotted with any antibody, but rather it serves to demonstrate the absence of non-specific reactions and the complete removal of unbound red blood cells form the test area. The spotted units were dried at 37° C. for 30 minutes. The dried units were stored at 25° C. with desiccant capsules (Dricap, Multiform Desiccants, Inc.).

Blood samples from two donors were collected in EDTA anticoagulant. Five drops (100–125 ul) of whole blood were added to the center sample application well. This ensured a sufficient volume of blood to flow laterally past the antibody spotted regions. Following a 1.5 minute incubation at 25° C., 26–30 drops (approximately 0.60–0.75 ml) of wash reagent were added to the center sample application well. This caused the unbound cells to flow from the antibody spotted region to the absorbent region of the porous plastic block.

Assay specificity was tested by preparation of packed red blood cells from aliquots of each test sample to remove the Apolipoprotein B serum components. The remaining packed red blood cells were washed with phosphate-buffered saline (PBS) and resuspended in varying amounts of Apolipoprotein B free serum (Scantibodies Laboratories, Lot 753A). These replacement study samples were subsequently tested according to the procedure described above.

Comparative studies were performed with a commercially available RIA product. A positive reaction was characterized by a red dot at the site of antibody application. This results when the porous plastic affixed antibody recognizes and binds the Apolipoprotein B serum component. The resulting lattice network which is formed as a result of this binding serves to entrap the red blood cells in the test sample. A negative reaction is identified as a clear or white region at the antibody application site.

Results

| Donor Test Sample | RIA Value mg/dl* | RBC Lateral Flow Titer** |
|---|---|---|
| KR-whole blood | 58 | 1:8 |
| 100% replacement | 20 | 1:2 |
| 50% replacement | 40 | 1:4 |
| KV-whole blood | 60 | 1:8 |
| 100% replacement | 10 | Undiluted |

*As determined by Ventrex Apo B RIA kit, Lot 0167
**Based on the highest dilution of Sheep Anti-Apolipoprotein B giving a positive reaction comparable to the positive control reaction.

The results show that the assay can be made semi-quantitative by using varying concentrations (in this case serial dilutions) of the specific binding reagent in the indicator zone. Higher amounts of analyte are detected by more dilute antibody preparations.

The indicator zones can thus be graduated for detection and calibrated to obtain the semiquantitative measure of analyte. For example, as shown above, 1:8 dilution will detect 58-60 mg.dl apo B (and all higher concentrations); however, 1:4 dilution will detect 40 mg/dl, while the 1:8 dilution will not. Thus, the highest dilution at which reaction is detectable will give a measure of the concentration of analyte.

EXAMPLE 7

Assay for Group A Streptococcus

A. Fixation of Specific Binder to Indicator Zones

Three different approaches were developed for immobilizing antibody within the support matrix:

1. Antibody was concentrated by Amicon ultrafiltration or collodion bag, and applied directly to the intended indicator zone of a Porex porous plastic strip. The Porex was then dried.
2. Antibody was concentrated as above, biotinylated, and applied to the dried indicator zone containing affixed avidin, and then dried.
3. Polystyrene beads, adsorbed with antibody, were applied to the Porex to obtain an indicator zone in the form of a spot. The beads could also be sprayed onto the desired portion of the Porex, so that bars or lines could be used as indicator zones.

Details

A.1 In the first approach, a 10-20 ul spot of concentrated DEAE purified rabbit anti-Group A strep antibody at 10-30 mg/ml in 0.1 M Na$_2$CO$_3$ buffer, pH 9.5 was applied approximately ⅜" from the end of the Porex strip. The strip was dried for three hours at 37° C.

A.2 In the second approach, a 10-20 ul spot of avidin at 10 mg/ml in 0.1 M Na$_2$CO$_3$ buffer pH 9.5 was applied approximately ⅜" from the end of the Porex strip. The strip was dried for three hours at 37° C. A second spot of biotinylated rabbit anti-Group A strep antibody at 10-30 mg/ml was then applied to the avidin spot, and the strip again dried for three hours at 37° C.

A.3 In the third approach, polystyrene beads from Polysciences, Warrington, PA were used to adsorb polyclonal antihuman gonadotropin antibodies.

One volume of polystyrene bead suspension (0.2-1 u diameter, 2.5% solids) was added to two volumes of affinity purified polyclonal anti-hCG in 0.75 mg/ml in glycine buffered saline (0.1 M Glycine, 0.2 M NaCl, pH 8.2). The antibody bead suspension was mixed for 24 hours at 25° C., and then centrifuged in an Eppendorf model 5414 centrifuge for five minutes. The supernatant was discarded and the beads were suspended in blocking solution (0.1 M KPO$_4$ pH 7.2, 1% BSA, 0.02% NaN$_3$), mixed for three hours at 25° C., and the beads were again centrifuged as above, washed, mixed, and centrifuged twice with the blocking buffer. The beads were finally resuspended in the same buffer at a concentration of 1% solids based upon starting concentration.

A 20 ul spot of these antibody absorbed beads at 1% solids was spotted on to the Porex strip approximately ⅜" from the end of the strip. The beads were dried for three hours at 37° C.

B. Assay for Streptococcus A Using Enzyme Detection

A 500 ul suspension of nitrous acid extracted Group A streptococcus was prepared by treating the equivalent of $5 \times 10^5$ bacteria with 2 M nitrous acid for one minute, and neutralizing with 0.75 M NaOH, 0.5 M Tris. To this suspension was added 100 ul of a conjugate of rabbit anti-Group A streptococcus which had been partially purified over DEAE cellulose (DE52, Whatman) and conjugated to alkaline phosphatase. The mixture was applied dropwise to the end of a Porex strip. The strip contained an indicator zone to which was affixed antistreptococcus A. Fixation was as described in Section A above. The sample was allowed to flow laterally past the immobilized antibody (indicator zone) spot and into an absorbent pad at the end of the strip.

The strip was incubated for 2-3 minutes, and washed by applying 1 ml of borate-saline-TWEEN TM detergent wash buffer (2 ml/l TWEEN TM detergent 20; 0.477 g/l Na borate . 10 H$_2$O; 0.309 g/l boric acid; 0.2 g/l Na azide; 23.3 g/l NaCl). The buffer was added dropwise to the end of the strip to flow laterally past the indicator zone into the absorbent pad. The bound streptococcus A was detected by applying 0.5 ml of alkaline phosphatase chromogen (2.1 mg/ml 5-bromo-chloro3-indolylphosphate, p-toluidine salt, pH 10.1 in 26.7 g/l aqueous aminomethyl propanol) to the end of the strip to flow laterally past the indicator zone. After 1-2 minutes incubation, the results were read; blue color signifying positive response, no color as a negative response.

EXAMPLE 8

Assay for hCG

A solution of hCG was prepared as a 500 ul sample containing 50 mIU hCG in buffered saline or urine. To this was added 100 ul of a conjugate of monoclonal anti-hCG which had been partially purified over DEAE celluose and conjugated to alkaline phosphatase. The mixture was applied dropwise to the end of a Porex porous plastic strip containing an indicator zone with affixed anti-hCG antibody prepared as in Preparation A.3 of Example 7. The sample was allowed to flow laterally past the antibody absorbed bead spot (indicator zone) and into an absorbent pad at the end of the strip. After incubating the strip for 2-3 minutes, the strip was washed by applying 1 ml of borate-saline-TWEEN TM detergent wash buffer dropwise to the end of the strip to flow laterally past the indicator zone into the absorbent pad. As above, 0.5 ml of alkaline phosphatase chromogen was applied to the end of the strip to flow laterally past the indicator zone. The results were read 1-2 minutes after incubation, blue color signifying positive response, no color signifying a negative response.

Industrial Application

This invention finds application in basic and clinical research medicine, immunology, and the like, in forensic science, and in the biochemical and biological industries generally.

We claim:

1. Apparatus for determining the presence or absence or the approximate amount of an analyte in a liquid sample which method comprises:
  a non-bibulous lateral flow membrane; wherein said membrane has on its surface;
  a liquid sample application zone defined to receive said liquid sample;
  at least one indicator zone spaced laterally apart from the application zone on said surface, wherein immobilized in said indicator zone is a member of a binding pair capable of binding said analyte or a derivative of said analyte; and
  wherein the lateral spacing of the application zone and the indicator zone is configured so as to cause the liquid sample introduced at the application zone to flow by non-bibulous lateral flow through the indicator zone;
  so as to permit the immobilized member to react with said analyte or derivative thereof so that the presence or absence or approximate amount of analyte is determined in the indicator zone.

2. The apparatus of claim 1 which further includes an absorption zone in lateral contact with said indicator zone so as to cause said liquid sample to flow through the indicator zone and into the absorption zone.

3. The apparatus of claim 2 wherein the absorption zone comprises a contiguous portion of the non-bibulous lateral flow membrane.

4. The apparatus of claim 2 wherein the absorption zone comprises a bibulous absorption body in contact with the non-bibulous lateral flow membrane.

5. The apparatus of claim 1 wherein the membrane is elongated in the application zone and the indicator zone are linearly spaced along the non-bibulous lateral flow membrane.

6. The apparatus of claim 5 which comprises a multiplicity of indicator zones linearly spaced along the non-bibulous lateral flow membrane.

7. The apparatus of claim 1 which comprises a multiplicity of indicator zones spaced radially around the liquid sample application zone.

8. The apparatus of claim 7 wherein the indicator zones are equidistant from the liquid sample application zone.

9. The apparatus of claim 1 wherein the member of the binding pair immobilized in the indicator zone is an antibody or fragment thereof.

10. The apparatus of claim 9 wherein the antibody or fragment thereof immobilized in the indicator zone is immunoreactive with a blood group antigen.

11. The apparatus of claim 1 wherein the member of the binding pair immobilized in the indicator zone is an antigen.

12. The apparatus of claim 1 which further contains a sample receiving pad in contact and on the top surface of the liquid sample application zone on the non-bibulous lateral flow membrane.

13. The apparatus of claim 12 wherein said sample receiving pad contains a reagent reactive with analyte to form a derivative of said analyte which derivative is reactive with the member of the binding pair that is immobilized in the indicator zone.

14. The apparatus of claim 13 wherein the reagent is an antibody or antigen or fragment thereof.

15. The apparatus of claim 1 which further comprises a breakable container of liquid reagent, said container positioned so as to release the reagent laterally through the non-bibulous lateral flow membrane and through the indicator zone without passing through the liquid sample application zone.

16. The apparatus of claim 15 which further includes a means to break said container.

17. An apparatus for measuring the presence or absence or approximate quantity of an analyte in a liquid sample which apparatus comprises, in combination:
  a non-bibulous lateral flow membrane;
  a housing for holding the membrane, said holding being so constructed as to form;
  means defining an application zone on the non-bibulous lateral flow membrane for receiving a liquid sample in said application zone;
  at least on indicator zone laterally apart from said application zone on said membrane to which is immobilized a member of a binding pair, said member being reactive with with analyte or a derivative or said analyte; and
  reading access means for permitting the indicator zone to be read, thus permitting measuring the presence or absence or approximate quantity of analyte by reading said indicator zone.

18. The apparatus of claim 17 which further comprises a bibulous absorbent body; and
  means for positioning a portion of the non-bibulous lateral flow membrane into contact with the absorbent body for permitting liquid to flow from the membrane to the absorbent body.

19. The apparatus of claim 17 further comprising a sample receiving pad on top of and contacting the liquid sample application zone.

20. The apparatus of claim 19 wherein said sample receiving pad contains a reagent capable of reacting with analyte to form a derivative of said analyte which is reactive with the member of the binding pair that is immobilized in the indicator zone.

21. The apparatus of claim 17 further comprising:
  at least one breakable container of liquid reagent,
  said container positioned to permit liquid to flow from the container, upon being broken in use, into the non-bibulous lateral flow membrane and through the indicator zone without passing through the liquid sample application zone.

22. A method for determining the presence or approximate amount of analyte in a sample comprising the steps of:
  placing the sample on the liquid sample application zone of a non-bibulous lateral flow membrane which comprises a liquid sample application zone and at least one indicator zone spaced apart from said application zone laterally on the surface of said membrane, there being immobilized in said indicator zone a member of a binding pair capable of binding the analyte or a derivative thereof, said sample being of sufficient quantity to cause sample liquid to flow laterally from the application zone through said indicator zone to permit the binding of analyte or derivative thereof with the member of the binding pair immobilized in the indicator zone; and assessing the binding of the analyte or derivative thereof in the indicator zone, to determine the presence, absence or approximate amount of analyte.

23. The method of claim 22 wherein the member of the binding pair immobilized in the indicator zone is an antibody or fragment thereof and the analyte is an antigen which contains an epitope reactive with the antibody or fragment thereof.

24. The method of claim 23 wherein the antigen is a soluble antigen.

25. The method of claim 24 wherein the antigen is selected from the group consisting of, tissue-specific cell surface markers, tissue-shared cell surface markers, viral-associated cell surface markers, tumor-specific cell surface markers, bacterial polysaccharides, viral coat proteins, hormones, drugs, and antibodies.

26. The method of claim 24 wherein the antigen is selected from the group consisting of apolipoprotein B and apolipoprotein A1.

27. The method of claim 23 wherein the antigen is bound to the surface of a particle.

28. The method of claim 27 wherein the particle is a cell.

29. The method of claim 27 wherein the particle is selected from the group consisting of red blood cells, platelets, tumor cells, bacteria, viruses, and viral particles.

30. The method of claim 29 wherein the particle is a red blood cell.

31. The method of claim 22 wherein the derivative of the analyte is a conjugate of said analyte with a member complementary to the member of the binding pair immobilized in the indicator zone.

32. The method of claim 31 wherein the member conjugated to analyte is further conjugated to label.

33. The method of claim 31 wherein said member complementary to the binding member immobilized in the indicator zone is applied to the application zone along with the analyte so as to effect conjugation of said member to the analyte in the application zone.

34. A method to detect the formation of a specific binding pair complex in an indicator zone of a non-bibulous lateral flow membrane said membrane having a pore size of 1-250 microns and having on its surface a liquid sample application zone defined to receive said liquid sample and at least one indicator zone spaced laterally apart from the application zone; wherein immobilized in said indicator zone is a member of a binding pair bound to its a complementary member of said binding pair so as to form a complex, which method comprises applying to the surface of said membrane detectable particles of sufficient size to be entrapped by said complex and causing said particles to flow laterally through said indicator zone, and detecting the presence of the particles in the indicator zone as a means of detecting the formation of the specific binding pair complex.

35. The method of claim 34 wherein the particles are red blood cells.

36. The method of claim 34 wherein the particles are colored latex.

37. The method of claim 34 wherein said detectable particles are present in a sample providing an analyte, which analyte is a member of said complex.

38. The method of claim 37 wherein said sample is whole blood.

39. A method for determining the presence or absence or approximate amount of an analyte in a liquid sample comprising the steps of:

applying the sample to the liquid sample application zone of a non-bibulous lateral flow membrane having a pore size of 1-250 microns which membrane comprises said application zone and at least one indicator zone spaced laterally apart from said application zone on the surface of said membrane, there being immobilized in said indicator zone a member of a binding pair capable of binding the analyte or a derivative thereof, said sample being of sufficient quantity to cause sample liquid to flow laterally from the application zone through said indicator zone; and detecting the binding of the analyte or derivative thereof in the indicator zone;

wherein said detecting is effected by entrapping detectable particles in a complex formed by the binding of the analyte or derivative thereof with the member of the binding pair immobilized in the indicator zone; and assessing the entrapment of the particles in the indicator zone to determine the presence or absence of approximate amount of analyte.

40. The method of claim 39 wherein the particles are added to the liquid sample before said sample is applied to the application zone.

41. The method of claim 39 wherein the particles are suspended in liquid and applied to the liquid sample application zone after the sample has been applied to said application zone.

42. The method of claim 39 wherein the particles are present in the sample.

43. The method of claim 39 wherein the particles are red blood cells.

44. The method of claim 39 wherein the particles are colored latex particles.

45. A method of type blood, which method comprises applying a sample of whole blood to the liquid sample application zone of a non-bibulous lateral flow membrane, wherein the membrane comprises:

said application zone defined to receive said whole blood sample, and at least one indicator zone spaced laterally apart from the application zone, said indicator zone having immobilized therein an antibody or fragment thereof immunoreactive with a blood typing antigen, said whole blood sample being of sufficient volume to permit the whole blood to flow through the indicator zone, and applying sufficient clear liquid to the membrane at a position apart from the indicator zone so as to laterally flow through the indicator zone to remove unbound reed blood cells from said indicator zone and detecting the presence or absence of red color in the indicator zone so as to determine the presence or absence of a blood typing antigen immunoreactive with the antibody or fragment thereof immobilized in the indicator zone.

46. The method of claim 45 wherein the membrane comprises an indicator zone in which is immobilized an antibody or fragment thereof having reactivity with group A antigen and an indicator zone in which is immobilized an antibody or fragment thereof having reactivity with group B antigen.

* * * * *

UNITED STATES PATENT AND TRADEMARK OFFICE
CERTIFICATE OF CORRECTION

PATENT NO. : 4,943,522

DATED : July 24, 1990

INVENTOR(S) : Robert W. Eisinger, Mohammed H. Khalil, David H. Katz, Robert B. Sargeant It is certified that error appears in the above-identified patent and that said Letters Patent is hereby corrected as shown below:

In column 29, line 20, after the word "which" and before the word "comprises", please delete the word "method".

In column 29, line 22, after the word "surface", please delete ";" and substitute --:--.

Signed and Sealed this

Twenty-first Day of January, 1992

*Attest:*

HARRY F. MANBECK, JR.

*Attesting Officer*     *Commissioner of Patents and Trademarks*